(12) United States Patent
Nau, Jr.

(10) Patent No.: US 11,647,907 B2
(45) Date of Patent: May 16, 2023

(54) SURGICAL DEVICES AND METHODS UTILIZING OPTICAL COHERENCE TOMOGRAPHY (OCT) TO MONITOR AND CONTROL TISSUE SEALING

(71) Applicant: Covidien LP, Mansfield, MA (US)

(72) Inventor: William H. Nau, Jr., Longmont, CO (US)

(73) Assignee: Covidien LP, Mansfield, MA (US)

( * ) Notice: Subject to any disclaimer, the term of this patent is extended or adjusted under 35 U.S.C. 154(b) by 74 days.

(21) Appl. No.: 17/462,207

(22) Filed: Aug. 31, 2021

(65) Prior Publication Data

US 2021/0393135 A1    Dec. 23, 2021

Related U.S. Application Data

(63) Continuation of application No. 16/275,913, filed on Feb. 14, 2019, now Pat. No. 11,103,135, which is a
(Continued)

(51) Int. Cl.
*A61B 5/00* (2006.01)
*A61B 18/14* (2006.01)
(Continued)

(52) U.S. Cl.
CPC .......... *A61B 5/0084* (2013.01); *A61B 5/0066* (2013.01); *A61B 18/1445* (2013.01);
(Continued)

(58) Field of Classification Search
CPC ....................... A61B 5/0066; A61B 2090/3735
See application file for complete search history.

(56) References Cited

U.S. PATENT DOCUMENTS

| D249,549 S | 9/1978 | Pike |
|---|---|---|
| D263,020 S | 2/1982 | Rau, III |
| (Continued) | | |

FOREIGN PATENT DOCUMENTS

| CN | 201299462 Y | 9/2009 |
|---|---|---|
| DE | 2415263 A1 | 10/1975 |
| (Continued) | | |

OTHER PUBLICATIONS

Johannes de Boer et al., "Imaging Thermally Damaged Tissue by Polarization Sensitive Optical Coherence Tomography", Optics Express, Sep. 14, 1998, vol. 3,No. 6, pp. 212-218.
(Continued)

*Primary Examiner* — Colin T. Sakamoto
(74) *Attorney, Agent, or Firm* — Carter, DeLuca & Farrell LLP

(57) ABSTRACT

Surgical devices and methods for utilizing optical coherence tomography (OCT) to monitor and control tissue sealing are disclosed. The surgical device includes an end effector assembly that includes first and second jaw members that are movable between a first, spaced-apart position and a second proximate position. An OCT system, at least a portion of which is incorporated into the end effector assembly, is configured to sense properties of the tissue, e.g., the structural density of the tissue, disposed between the first and second jaw members. A tissue-sealing energy source may be disposed within at least one of the jaw members and may provide tissue-sealing energy to tissue disposed between the jaw members. A controller, which is coupled to the OCT system and the tissue-sealing energy source, controls the tissue-sealing energy generated by the tissue-sealing energy source based on the properties of the tissue sensed by the OCT system.

17 Claims, 9 Drawing Sheets

Related U.S. Application Data continuation of application No. 14/052,827, filed on Oct. 14, 2013, now Pat. No. 10,206,583.

(60) Provisional application No. 61/720,817, filed on Oct. 31, 2012.

(51) Int. Cl.
  *A61B 17/32* (2006.01)
  *A61B 18/00* (2006.01)
  *A61B 90/00* (2016.01)

(52) U.S. Cl.
  CPC .............. *A61B 2017/320093* (2017.08); *A61B 2017/320094* (2017.08); *A61B 2017/320095* (2017.08); *A61B 2018/0063* (2013.01); *A61B 2018/00642* (2013.01); *A61B 2090/3735* (2016.02)

(56) References Cited

U.S. PATENT DOCUMENTS

| | | |
|---|---|---|
| D295,893 S | 5/1988 | Sharkany et al. |
| D295,894 S | 5/1988 | Sharkany et al. |
| D298,353 S | 11/1988 | Manno |
| D299,413 S | 1/1989 | DeCarolis |
| D343,453 S | 1/1994 | Noda |
| D348,930 S | 7/1994 | Olson |
| D349,341 S | 8/1994 | Lichtman et al. |
| D354,564 S | 1/1995 | Medema |
| D358,887 S | 5/1995 | Feinberg |
| D384,413 S | 9/1997 | Zlock et al. |
| 5,772,597 A | 6/1998 | Goldberger et al. |
| H1745 H | 8/1998 | Paraschac |
| D402,028 S | 12/1998 | Grimm et al. |
| D408,018 S | 4/1999 | McNaughton |
| D416,089 S | 11/1999 | Barton et al. |
| D424,694 S | 5/2000 | Tetzlaff et al. |
| D425,201 S | 5/2000 | Tetzlaff et al. |
| H1904 H | 10/2000 | Yates et al. |
| 6,201,608 B1 | 3/2001 | Mandella |
| D449,886 S | 10/2001 | Tetzlaff et al. |
| 6,343,227 B1 | 1/2002 | Crowley |
| D453,923 S | 2/2002 | Olson |
| D454,951 S | 3/2002 | Bon |
| D457,958 S | 5/2002 | Dycus et al. |
| D457,959 S | 5/2002 | Tetzlaff et al. |
| H2037 H | 7/2002 | Yates et al. |
| D465,281 S | 11/2002 | Lang |
| D466,209 S | 11/2002 | Bon |
| 6,485,413 B1 | 11/2002 | Boppart et al. |
| D493,888 S | 8/2004 | Reschke |
| D496,997 S | 10/2004 | Dycus et al. |
| D499,181 S | 11/2004 | Dycus et al. |
| D502,994 S | 3/2005 | Blake, III |
| D509,297 S | 9/2005 | Wells |
| D525,361 S | 7/2006 | Hushka |
| D531,311 S | 10/2006 | Guerra et al. |
| D533,274 S | 12/2006 | Visconti et al. |
| D533,942 S | 12/2006 | Kerr et al. |
| D535,027 S | 1/2007 | James et al. |
| D538,932 S | 3/2007 | Malik |
| D541,418 S | 4/2007 | Schechter et al. |
| D541,611 S | 5/2007 | Aglassinge |
| D541,938 S | 5/2007 | Kerr et al. |
| D545,432 S | 6/2007 | Watanabe |
| D547,154 S | 7/2007 | Lee |
| D564,662 S | 3/2008 | Moses et al. |
| D567,943 S | 4/2008 | Moses et al. |
| D575,395 S | 8/2008 | Hushka |
| D575,401 S | 8/2008 | Hixson et al. |
| D582,038 S | 12/2008 | Swoyer et al. |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| D621,503 S | 8/2010 | Otten et al. |
| D627,462 S | 11/2010 | Kingsley |
| D628,289 S | 11/2010 | Romero |
| D628,290 S | 11/2010 | Romero |
| D630,324 S | 1/2011 | Reschke |
| D649,249 S | 11/2011 | Guerra |
| D649,643 S | 11/2011 | Allen, IV et al. |
| D661,394 S | 6/2012 | Romero et al. |
| 10,206,583 B2 | 2/2019 | Nau, Jr. |
| 11,103,135 B2 | 8/2021 | Nau, Jr. |
| 2002/0166946 A1 | 11/2002 | Iizuka et al. |
| 2005/0203504 A1 | 9/2005 | Wham et al. |
| 2006/0015165 A1 | 1/2006 | Bertolero et al. |
| 2007/0055117 A1 | 3/2007 | Alphonse |
| 2007/0197874 A1 | 8/2007 | Ishihara |
| 2007/0270792 A1 | 11/2007 | Hennemann et al. |
| 2009/0177094 A1 | 7/2009 | Brown et al. |
| 2010/0249769 A1* | 9/2010 | Nau, Jr. .............. A61B 18/18 606/33 |
| 2011/0222070 A1* | 9/2011 | Nagai ................ A61B 5/0066 356/496 |
| 2011/0251605 A1 | 10/2011 | Hoarau et al. |
| 2011/0279821 A1 | 11/2011 | Brennan |
| 2011/0282190 A1 | 11/2011 | Caffey et al. |
| 2012/0253328 A1 | 10/2012 | Cunningham et al. |
| 2013/0345558 A1 | 12/2013 | Boppart |
| 2015/0224326 A1 | 8/2015 | Toth |

FOREIGN PATENT DOCUMENTS

| | | |
|---|---|---|
| DE | 02514501 A1 | 10/1976 |
| DE | 2627679 A1 | 1/1977 |
| DE | 03423356 C2 | 6/1986 |
| DE | 03612646 A1 | 4/1987 |
| DE | 8712324 U1 | 2/1988 |
| DE | 04303882 C2 | 2/1995 |
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19738457 A1 | 3/1999 |
| DE | 19751108 A1 | 5/1999 |
| DE | 19946527 C1 | 7/2001 |
| DE | 20121161 U1 | 4/2002 |
| DE | 10045375 C2 | 10/2002 |
| DE | 10249674 A1 | 5/2004 |
| DE | 202007009165 U1 | 8/2007 |
| DE | 202007009317 U1 | 8/2007 |
| DE | 202007009318 U1 | 8/2007 |
| DE | 10031773 B4 | 11/2007 |
| DE | 202007016233 U1 | 1/2008 |
| DE | 102004026179 B4 | 1/2009 |
| DE | 102008018406 B3 | 7/2009 |
| EP | 1281878 A1 | 2/2003 |
| EP | 1159926 A2 | 3/2003 |
| EP | 2174613 A1 | 4/2010 |
| EP | 2241280 A2 | 10/2010 |
| JP | 61501068 A | 5/1986 |
| JP | 1024051 A | 1/1989 |
| JP | 1147150 A | 6/1989 |
| JP | 55106 | 1/1993 |
| JP | 0540112 | 2/1993 |
| JP | 0006030945 | 2/1994 |
| JP | 6121797 A | 5/1994 |
| JP | 6285078 A | 10/1994 |
| JP | 06343644 | 12/1994 |
| JP | 6511401 | 12/1994 |
| JP | 07265328 | 10/1995 |
| JP | 856955 | 3/1996 |
| JP | 08252263 A | 10/1996 |
| JP | 8289895 A | 11/1996 |
| JP | 8317934 A | 12/1996 |
| JP | 8317936 A | 12/1996 |
| JP | 910223 A | 1/1997 |
| JP | 09000538 A | 1/1997 |

(56) References Cited

FOREIGN PATENT DOCUMENTS

| | | |
|---|---|---|
| JP | 9122138 A | 5/1997 |
| JP | 0010000195 A | 1/1998 |
| JP | 10155798 A | 6/1998 |
| JP | 11070124 A | 3/1999 |
| JP | 11169381 A | 6/1999 |
| JP | 11192238 A | 7/1999 |
| JP | 11244298 | 9/1999 |
| JP | 2000102545 A | 4/2000 |
| JP | 2000135222 A | 5/2000 |
| JP | 2000342599 A | 12/2000 |
| JP | 2000350732 A | 12/2000 |
| JP | 2001008944 A | 1/2001 |
| JP | 2001029356 A | 2/2001 |
| JP | 2001003400 | 4/2001 |
| JP | 2001128990 A | 5/2001 |
| JP | 2001190564 A | 7/2001 |
| JP | 2002136525 A | 5/2002 |
| JP | 2002528166 A | 9/2002 |
| JP | 2003116871 A | 4/2003 |
| JP | 2003175052 A | 6/2003 |
| JP | 2003245285 A | 9/2003 |
| JP | 2004517668 A | 6/2004 |
| JP | 2004528869 A | 9/2004 |
| JP | 2005152663 A | 6/2005 |
| JP | 2005253789 A | 9/2005 |
| JP | 2006015078 A | 1/2006 |
| JP | 2006501939 A | 1/2006 |
| JP | 2006095316 A | 4/2006 |
| JP | 2011125195 A | 6/2011 |
| JP | 6502328 B2 | 4/2019 |
| SU | 401367 A1 | 10/1973 |
| WO | 0036986 A1 | 6/2000 |
| WO | 0059392 A1 | 10/2000 |
| WO | 0115614 A1 | 3/2001 |
| WO | 0154604 A1 | 8/2001 |
| WO | 0245589 A2 | 6/2002 |
| WO | 2006021269 A1 | 3/2006 |
| WO | 2005110264 A2 | 4/2006 |
| WO | 2008040483 A1 | 4/2008 |
| WO | 20090005850 A1 | 1/2009 |
| WO | 2011018154 A1 | 2/2011 |

OTHER PUBLICATIONS

Michael Choti, "Abdominoperineal Resection with the LigaSure Vessel Sealing System and LigaSure Atlas 20 cm Open Instrument" Innovations That Work, Jun. 2003.

Chung et al., "Clinical Experience of Sutureless Closed Hemorrhoidectomy with LigaSure" Diseases of the Colon & Rectum vol. 46, No. 1 Jan. 2003.

Tinkcler L.F., "Combined Diathermy and Suction Forceps", Feb. 6, 1967 (Feb. 6, 1965), British Medical Journal Feb. 6, 1976, vol. 1, nr. 5431 p. 361, ISSN: 0007-1447.

Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas MedicalCenter,Charlotte,NC; Date: Aug. 2003.

Peterson et al., "Comparison of Healing Process Following Ligation with Sutures and Bipolar Vessel Sealing" Surgical Technology International (2001).

"Electrosurgery: A Historical Overview". Innovations in Electrosurgery; Sales/Product Literature; Dec. 31, 2000.

Johnson et al. "Evaluation of a Bipolar Electrothermal Vessel Sealing Device in Hemorrhoidectomy" Sales/Product Literature; Jan. 2004.

E. David Crawford, "Evaluation of a New Vessel Sealing Device in Urologic Cancer Surgery" Sales/Product Literature 2000.

Johnson et al. "Evaluation of the LigaSure Vessel Sealing System in Hemorrhoidectormy" American College of Surgeons (ACS) Clinicla Congress Poster (2000).

Muller et al. "Extended Left Hemicolectomy Using the LigaSure Vessel Sealing System" Innovations That Work; Sep. 1999.

Kennedy et al. "High-burst-strength, feedback-controlled bipolar vessel sealing" Surgical Endoscopy (1998) 12:876-878.

Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.

Carus et al., "Initial Experience With the LigaSure Vessel Sealing System in Abdominal Surgery" Innovations That Work,Jun. 2002.

Heniford et al. "Initial Research and Clinical Results with an Electrothermal Bipolar Vessel Sealer" Oct. 1999.

Heniford et al. "Initial Results with an Electrothermal Bipolar Vessel Sealer" Surgical Endoscopy (2000) 15:799-801.

Herman et al., "Laparoscopic Intestinal Resection With the LigaSure Vessel Sealing System: A Case Report" Innovations That Work, Feb. 2002.

Koyle et al., "Laparoscopic Palomo Varicocele Ligation in Children and Adolescents" Pediatric Endosurgery & Innovative Techniques, vol. 6, No. 1, 2002.

W. Scott Helton, "LigaSure Vessel Sealing System: Revolutionary Hemostasis Product for General Surgery"; Sales/Product Literature 1999.

LigaSure Vessel Sealing System, the Seal of Confidence in General, Gynecologic, Urologic, and Laparaoscopic Surgery; Sales/Product Literature; Apr. 2002.

Joseph Ortenberg "LigaSure System Used in Laparoscopic 1st and 2nd Stage Orchiopexy" Innovations That Work, 2002.

Sigel et al., "The Mechanism of Blood Vessel Closure by High Frequency Electrocoagulation" Surgery Gynecology & Obstetrics, Oct. 1965 pp. 823-831.

Sampayan et al, "Multilayer Ultra-High Gradient Insulator Technology" Discharges and Electrical Insulation in Vacuum, 1998. Netherlands Aug. 17-21, 1998; vol. 2, pp. 740-743.

Paul G. Horgan, "A Novel Technique for Parenchymal Division During Hepatectomy" The American Journal of Surgery, vol. 181, No. 3, Apr. 2001 pp. 236-237.

Benaron et al., "Optical Time-of-Flight and Absorbance Imaging of Biologic Media", Science, American Association for the Advancement of Science, Washington, DC, vol. 259, Mar. 5, 1993, pp. 1463-1466.

Olsson et al. "Radical Cystectomy in Females". Current Surgical Techniques in Urology, vol. 14, Issue 3, 2001.

Palazzo et al. "Randomized clinical trial of Ligasure versus open haemorrhoidectomy" British Journal of Surgery 2002, 89, 154-157.

Levy et al. "Randomized Trial of Suture Versus Electrosurgical Bipolar Vessel Sealing in Vaginal Hysterectomy" Obstetrics & Gynecology, vol. 102, No. 1, Jul. 2003.

Bergdahl et al., "Studies on Coagulation and the Development of an Automatic Computerized Bipolar Coagulator" J. Neurosurg, vol. 75, Jul. 1991, pp. 148-151.

Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.

Sayfan et al., "Sutureless Closed Hemorrhoidectomy: A New Technique" Annals of Surgery, vol. 234, No. 1, Jul. 2001, pp. 21-24.

Levy et al., "Update on Hysterectomy—New Technologies and Techniques" OBG Management, Feb. 2003.

Dulemba et al. "Use of a Bipolar Electrothermal Vessel Sealer in Laparoscopically Assisted Vaginal Hysterectomy" Sales/Product Literature; Jan. 2004.

Sengupta et al., "Use of a Computer-Controlled Bipolar Diathermy System in Radical Prostatectomies and Other Open Urological Surgery" ANZ Journal of Surgery (2001)71.9 pp. 538-540.

Rothenberg et al. "Use of the LigaSure Vessel Sealing System in Minimally Invasive Surgery in Children" Int'l Pediatric Endosurgery Group (IPEG) 2000.

Crawford et al. "Use of the LigaSure Vessel Sealing System in Urologic Cancer Surgery"; Grand Rounds in Urology 1999 vol. 1 Issue 4 pp. 10-17.

Craig Johnson, "Use of the LigaSure Vessel Sealing System in Bloodless Hemorrhoidectomy"; Innovations That Work, Mar. 2000.

(56) References Cited

OTHER PUBLICATIONS

Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford, "Use of a Novel Vessel Sealing Technology in Management of the Dorsal Veinous Complex" Sales Product Literature 2000.
Jarrett et al., "Use of the LigaSure Vessel Sealing System for Peri-Hilar Vessels in Laparoscopic Nephrectomy"; Sales/Product Literature 2000.
Crouch et al. "A Velocity-Dependent Model for Needle Insertion in Soft Issue"; MICCAI 2005; LNCS 3750 pp. 624-632, Dated: 2005.
McLellan et al., "Vessel Sealing for Hemostasis During Pelvic Surgery" Int'l Federation of Gynecology and Obstetrics Figo World Congress 2000, Washington, DC.
McLellan et al. "Vessel Sealing for Hemostasis During Gynecologic Surgery" Sales/Product Literature 1999.
"Reducing Needlestick Injuries in the Operating Room"; Sales/Product Literature 2001.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
European Search Report dated Oct. 10, 2016, issued in EP Application No. 16176334.7.

\* cited by examiner

SURGICAL DEVICES AND METHODS UTILIZING OPTICAL COHERENCE TOMOGRAPHY (OCT) TO MONITOR AND CONTROL TISSUE SEALING

CROSS REFERENCE TO RELATED APPLICATION

The present application is a continuation of U.S. patent application Ser. No. 16/275,913, filed on Feb. 14, 2019, which is a continuation of U.S. patent application Ser. No. 14/052,827, filed on Oct. 14, 2013, now U.S. Pat. No. 10,206,583, which claims the benefit of and priority to U.S. Provisional Patent Application Ser. No. 61/720,817, filed on Oct. 31, 2012. The entire contents of each of the foregoing applications are hereby incorporated herein by reference.

BACKGROUND

Technical Field

The present disclosure relates to surgical forceps having optical components for monitoring and controlling tissue sealing. More particularly, the present disclosure relates to open or endoscopic forceps that incorporates Optical Coherence Tomography (OCT) system components to monitor and to provide feedback for controlling a tissue sealing.

Description of Related Art

Existing energy-based tissue-sealing surgical forceps use different types of energy to heat tissue. The different types of energy used to heat tissue include direct heat conduction from a heating element, RF current, ultrasound, and light. A typical energy-based tissue-sealing surgical forceps includes jaw members for grasping and compressing the tissue and applying energy to the tissue.

During a surgical procedure, it is important for a surgeon to be able to determine the status of a tissue seal, e.g., the quality of a tissue seal. This feedback allows a surgeon to appropriately operate the tissue-sealing surgical forceps to create a high-quality tissue seal. Existing tissue-sealing surgical forceps and associated systems may not provide sufficient information about the status of a tissue seal.

SUMMARY

As used herein, the term "distal" refers to that portion that is further from an operator while the term "proximal" refers to that portion that is closer to an operator. As used herein, the term "treat" refers to performing a surgical treatment to tissue including, but not limited to heating, sealing, cutting, sensing, and/or monitoring.

As used herein, the term "light source" broadly refers to all types of devices or elements that generate or transmit light for medical use (e.g., tissue treatment). These devices include lasers, light emitting diodes (LEDs), lamps, and other devices that generate light having a wavelength that is within the light spectrum (e.g., from infrared light to ultraviolet light). Also, the light sources described herein may be used interchangeably. For example, an LED light source may be used interchangeably with a laser light source.

As described in more detail below with reference to the accompanying figures, the present disclosure relates to open or endoscopic surgical forceps that incorporates optical and electrical components for performing Optical Coherence Tomography (OCT) to image tissue for diagnostic or identification purposes, or to image a tissue seal after a tissue sealing cycle to determine the quality of the tissue seal. In some embodiments, the optical components use broadband, infrared light having a wavelength of between 800 and 1550 nm to image subsurface tissue structures at depths of a few millimeters and with a resolution on the order of micrometers.

The optical components may include reference arm optics disposed in a first jaw member of the surgical forceps and sample arm optics disposed in a second jaw member opposite the first jaw member. The optical components also include a light source configured to generate broadband light and transmit the broadband light to the reference arm and the sample arm. The optical components further include a light detector that detects an interference pattern in the broadband light that is reflected back from the reference arm optics and the sample arm optics. The electrical components may include a signal processor that processes the detected interference pattern and displays an image of the sealed tissue on a display device.

The optical components may further include a aiming light source for generating an aiming beam and an optical coupler that optically couples the aiming beam to the broadband light before the resulting light is transmitted to the reference arm optics and the sample arm optics.

The OCT system may incorporate polarization optics to measure birefringence to determine whether collagen has been denatured. In other embodiments, the OCT system may be configured to perform optical coherence microscopy using a high numerical aperture for histology or tissue diagnostics. The numerical aperture (NA) refers to the resolving power of a lens. Values of NA that are greater than 1.2 may be considered high. The optical resolution is proportional to $\lambda/(2\times NA)$, where $\lambda$ is the wavelength of the light.

The OCT system may be configured to perform color Doppler coherence tomography to measure tissue perfusion.

In one aspect, the present disclosure features a surgical device. The surgical device includes a housing and an end effector assembly operably coupled to the housing. The end effector assembly includes first and second jaw members that each have a tissue contacting surface. At least one of the first and second jaw members is movable between a first, spaced-apart position and a second proximate position. The end effector assembly further includes a sample arm optical assembly of an interferometer coupled to the first jaw member. The sample arm optical assembly transmits a first light beam to tissue grasped between the first and second jaw members and receives at least a portion of the first light beam reflected from the tissue.

The end effector assembly also includes a reference mirror of the interferometer coupled to the second jaw member. The end effector assembly further includes a reference arm optical assembly of the interferometer coupled to the second jaw member. The reference arm optical assembly transmits a second light beam to the reference mirror and receives at least a portion of the second light beam reflected from the reference mirror.

The sample arm optical assembly may include movable sample arm optics that scan the first light beam across the tissue. The sample arm optical assembly may include a light guide operable to translate and rotate with respect to a longitudinal axis of the first jaw member to scan the tissue.

The reference arm optical assembly may translate along a longitudinal axis of the second jaw member. Alternatively, the reference mirror may translate along a longitudinal axis of the second jaw member.

The first jaw member may be a top jaw member and the second jaw member may be a bottom jaw member.

The surgical device may further include an optical coupler optically coupled to the sample arm optical assembly and the reference arm optical assembly. The optical coupler may provide a first light beam through a first output of the optical coupler to the sample arm optical assembly and may provide a second light beam through a second output of the optical coupler to the reference arm optical assembly.

The surgical device may include an imaging light source that generates imaging light. The imaging light source may be optically coupled to an input of the optical coupler.

The surgical device may further include a visible light source that generates visible light and a second optical coupler having a first input, a second input, and an output. The first input of the second optical coupler may be optically coupled to the imaging light source and the second input of the second optical coupler may be optically coupled to the visible light source. The second optical coupler may combine the imaging light and the visible light and to transmit the combined light out of the output of the second optical coupler.

A portion of the housing of the surgical device may form a handle and the imaging light source and the visible light source may be disposed within the handle.

The sample arm optical assembly may include polarization optics to allow for birefringence. Alternatively, the sample arm optical assembly and the reference arm optical assembly may be configured for optical coherence microscopy using a high numerical aperture.

In another aspect, the present disclosure features a system for treating tissue. The system includes a surgical device and a processor. The surgical device includes a housing and an end effector assembly operably coupled to the housing. The end effector assembly includes first and second jaw members that each have a tissue contacting surface. At least one of the first and second jaw members is movable between a first, spaced-apart position and a second proximate position. The end effector assembly further includes a sample arm optical assembly of an interferometer coupled to the first jaw member. The sample arm optical assembly transmits a first light beam to tissue grasped between the first and second jaw members and receives at least a portion of the first light beam reflected from the tissue.

The end effector assembly also includes a reference mirror of the interferometer coupled to the second jaw member. The end effector assembly further includes a reference arm optical assembly of the interferometer coupled to the second jaw member. The reference arm optical assembly transmits a second light beam to the reference mirror and receives at least a portion of the second light beam reflected from the reference mirror.

The end effector assembly further includes a light detector that detects at least a portion of the first light beam reflected from the tissue and at least a portion of the second light beam reflected from the reference mirror and generates a light detection signal. The processor of the system for treating tissue is coupled to the light detector and is configured to process the light detection signal to obtain interference pattern data. The processor may be configured to generate an image signal based on the interference pattern data and to transmit the image signal to a display device.

The system may further include an energy source coupled to at least one of the first and second jaw members and a controller coupled to the light detector and the energy source. The energy source delivers energy to the at least one of the first and second jaw members to seal tissue and the controller controls the energy source based on the at least one measured property of the light energy passing through the tissue. At least one of the energy source and the controller may be disposed within the housing.

In yet another aspect, the present disclosure features a method of determining properties of tissue in an energy-based medical device. The method includes grasping tissue between first and second jaw members of an energy-based medical device by moving at least one of the first and second jaw members between a first, spaced-apart position and a second proximate position. The method further includes directing a first light beam to the tissue grasped between the first and second jaw members, receiving at least a portion of the first light beam reflected from the tissue, directing a second light beam to a reference mirror, receiving at least a portion of the second light beam reflected from the reference mirror, combining the at least a portion of the first light beam reflected from the tissue and the at least a portion of the second light beam reflected from the reference mirror to form an interference light beam, detecting the interference light beam, and determining at least one tissue property based upon the detected interference light beam.

Determining at least one tissue property may include forming an image of the tissue based upon the detected interference light beam. The method may further include controlling the energy applied to the tissue by the energy-based medical device based upon the at least one tissue property. The method may further include determining tissue seal quality, identifying the tissue, or diagnosing the tissue based upon the at least one tissue property.

In one aspect, the present disclosure features a surgical device. The surgical device includes a shaft, an end effector assembly operably coupled to the shaft, and a controller. The end effector assembly includes first and second jaw members, each of which has a tissue-contacting surface. At least one of the first and second jaw members is movable between a first, spaced-apart position and a second proximate position. The end effector assembly further includes a tissue-sealing energy source disposed within at least the first jaw member. The tissue-sealing energy source is configured to provide tissue-sealing energy to tissue disposed between the first and second jaw members.

The end effector assembly further includes an OCT probe configured to sense properties of tissue disposed between the first and second jaw members. The controller is coupled to the OCT probe and the tissue-sealing energy source so that the controller can control the tissue-sealing energy generated by the tissue-sealing energy source based upon the structural density of the vessel sensed by the OCT probe.

The OCT probe may be embedded within the second jaw member. Further, at least a portion of the tissue-contacting surface of the first jaw member may include a transparent optical element that allows light to pass between the OCT probe and the tissue. Still further, the tissue-sealing energy source may generate tissue-sealing light and a reflective element may be disposed on the surface of the transparent optical element to prevent the tissue-sealing light from passing through the transparent optical element.

The OCT probe may be rotatably coupled to the second jaw member so that the OCT probe moves between a position parallel to the longitudinal axis of the second jaw member to a position perpendicular to the longitudinal axis of the second jaw member. Alternatively, the OCT probe may be movably coupled to the shaft so that the OCT probe can move out of the shaft between the first and second jaw members.

The surgical device may further include a second tissue-sealing energy source disposed within the second jaw member. The second tissue-sealing energy source may be configured to provide tissue-sealing energy to tissue disposed between the first and second jaw members.

The tissue-sealing energy source may generate electrical energy or ultrasonic energy.

The controller may be configured to operate the OCT probe to sense a tissue property prior to activating the tissue-sealing energy source. The controller may be additionally or alternatively configured to operate the OCT probe to sense a tissue property while operating the tissue-sealing energy source.

The OCT probe may sense the structural density of the tissue disposed between the first and second jaw members. The controller may correlate the sensed structural density of the tissue to the amount of collagen contained within the tissue disposed between the first and second jaw members.

In another aspect, the present disclosure features a method of sealing tissue. The method includes grasping tissue between first and second jaw members of a surgical device, sensing the structural density of the tissue disposed between the first and second jaw members using an OCT probe, determining parameters for tissue-sealing energy based upon the structural density of the tissue sensed by the OCT probe, and providing the tissue-sealing energy to the tissue based upon the determined parameters of the tissue-sealing energy.

The method of sealing tissue may also include inserting the OCT probe in between the first and second jaw members so that the distal end of the OCT probe is close to the tissue after the tissue is grasped between the first and second jaw members. The method may further include retracting the OCT probe from in between the first and second jaw members after the OCT probe completes sensing the structural density of the tissue grasped between the first and second jaw members.

The method may include sensing the structural density of the tissue disposed between the first and second jaw members using an OCT probe after providing the tissue-sealing energy to the tissue, and determining the quality of the tissue seal based upon the sensed structural density of the tissue.

The method may include rotating the OCT probe from a first position parallel to the longitudinal axis of the second jaw member to a second position perpendicular to the longitudinal axis of the second jaw member prior to activating the OCT probe to sense the structural density of the grasped tissue.

The tissue-sealing energy may be electrical energy or ultrasonic energy. The method may include simultaneously operating the OCT probe to sense the structural density of the tissue and to provide tissue-sealing energy to the tissue. The method of sealing tissue may include correlating the sensed structural density of the grasped tissue to the amount of collagen and/or elastin contained within the grasped tissue.

BRIEF DESCRIPTION OF THE DRAWINGS

Various embodiments of the subject instrument are described herein with reference to the drawings wherein.

DETAILED DESCRIPTION

Figure 1A:
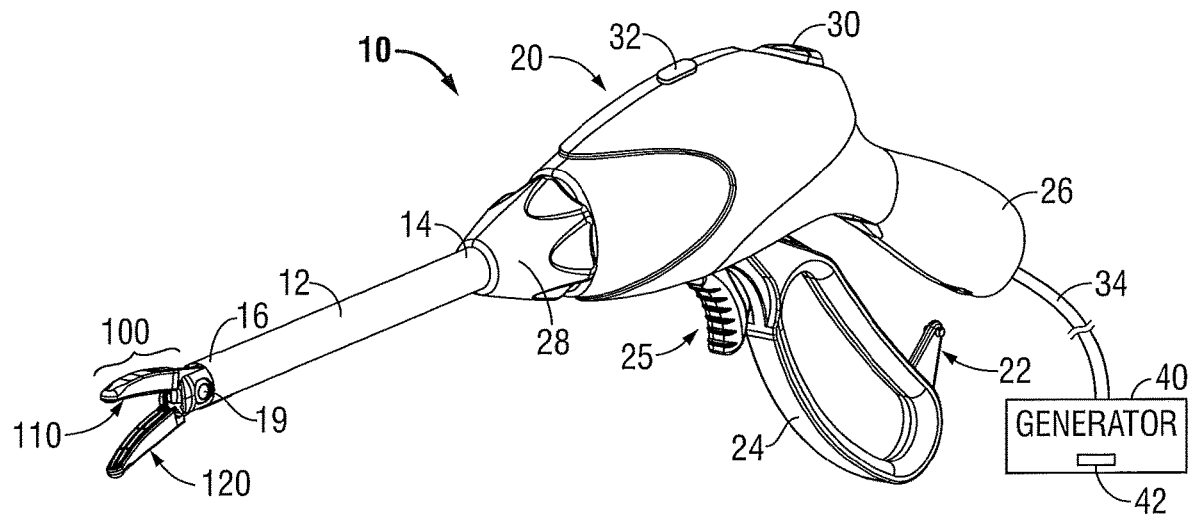
FIG. 1A is a perspective view of an endoscopic forceps having an end effector assembly, which incorporates all or a portion of the components of an OCT system, attached to a distal end of the forceps according to some embodiments of the present disclosure.

Embodiments of the presently-disclosed surgical instrument are described in detail with reference to the drawings wherein like reference numerals identify similar or identical elements.

FIG. 1A shows an endoscopic surgical forceps 10 that incorporates the OCT systems described below. In FIG. 1A, forceps 10 is coupled to an energy source (e.g., a generator 40) for generating energy, such as electrical energy, ultrasonic energy, or light energy configured to seal tissue. The energy source (e.g., generator 40) is configured to output energy having desired characteristics. Forceps 10 is coupled to the generator 40 via a cable 34 that is configured to transmit energy and control signals between the forceps 10 and the generator 40. Various embodiments of the forceps 10 using various types of energy are described below.

Forceps 10 is configured to support an end effector assembly 100. Forceps 10 includes various conventional features (e.g., a housing 20, a handle assembly 22, a trigger assembly 25, and a rotating assembly 28) that enable forceps 10 and end effector assembly 100 to mutually cooperate to grasp, seal, divide, and/or sense tissue. Forceps 10 generally includes a housing 20 and a handle assembly 22 that includes a moveable handle 24 and a handle 26 that is integral with housing 20. The handle 24 is moveable relative to the handle 26 to actuate end effector assembly 100 via a drive assembly (not shown) to grasp tissue.

In some embodiments, trigger assembly 25 may be configured to actuate a knife blade (not shown) or another component to sever tissue after a successful seal. Forceps 10 also includes a shaft 12 having a distal portion 16 that mechanically engages end effector assembly 100 and a proximal portion 14 that mechanically engages housing 20 proximate rotating assembly 28 disposed on housing 20. Rotating assembly 28 is mechanically associated with shaft 12 such that rotational movement of rotating assembly 28 imparts similar rotational movement to shaft 12 that, in turn, rotates end effector assembly 100.

End effector assembly 100 includes two jaw members 110, 120 having proximal ends and distal ends (see FIG. 1A). One or both jaw members 110, 120 are pivotable about a pin 19 and one or both jaw members 110, 120 are movable from a first position wherein jaw members 110, 120 are spaced relative to another, to a second position wherein jaw members 110, 120 are closed and cooperate to grasp tissue between the jaw members 110, 120.

Each jaw member 110, 120 includes a tissue contacting surface disposed on an inner-facing surface thereof (see FIG. 1A). Tissue-contacting surfaces cooperate to grasp and seal tissue held between the tissue-contacting surfaces. Tissue-contacting surfaces are connected to generator 40 that can transmit energy through the tissue held between the tissue-contacting surfaces.

First and second switch assemblies 30 and 32 are configured to selectively provide energy to end effector assembly 100. More particularly, the first switch assembly 30 may be configured to perform a first type of surgical procedure (e.g., seal, cut, and/or sense) and a second switch assembly 32 may be configured to perform a second type of surgical procedure (e.g., seal, cut, and/or sense). It should be noted that the presently-disclosed embodiments may include any number of suitable switch assemblies and are not limited to only switch assemblies 30 and 32. It should further be noted that the presently-disclosed embodiments may be configured to perform any suitable surgical procedure and are not limited to only sealing, cutting, and sensing.

The handle assembly 20 may further include one or more light transmissive elements, such as a cable or optical fibers 34 that connects the forceps 10 to the generator 40. The cable 34 may include a plurality of optical fibers to transmit light through various paths and ultimately to the OCT system incorporated into the end effector assembly 100, which is described in further detail below.

First and second switch assemblies 30 and 32 may also cooperate with a controller 42, which may be implemented by a logic circuit, a computer, a processor, and/or a field programmable gate array. The controller 42 may automatically trigger one of the switches to change between a first mode (e.g., sealing mode) and a second mode (e.g., cutting mode) upon the detection of one or more parameters or thresholds. In some embodiments, the controller 42 is also configured to receive various sensor feedback and to control the generator 40 based on the sensor feedback. The embodiments of the present disclosure allow the jaw members 110, 120 to seal and/or cut tissue using any suitable form of energy.

In some embodiments, the controller 42 may include a feedback loop that indicates when a tissue seal is complete based upon one or more of the following parameters: tissue temperature, optical sensing, change in impedance of the tissue over time and/or changes in the optical or electrical power or current applied to the tissue over time, rate of change of these properties and combinations thereof. An audible or visual feedback monitor may be employed to convey information to the surgeon regarding the overall seal quality or the completion of an effective tissue seal.

Figure 1B:
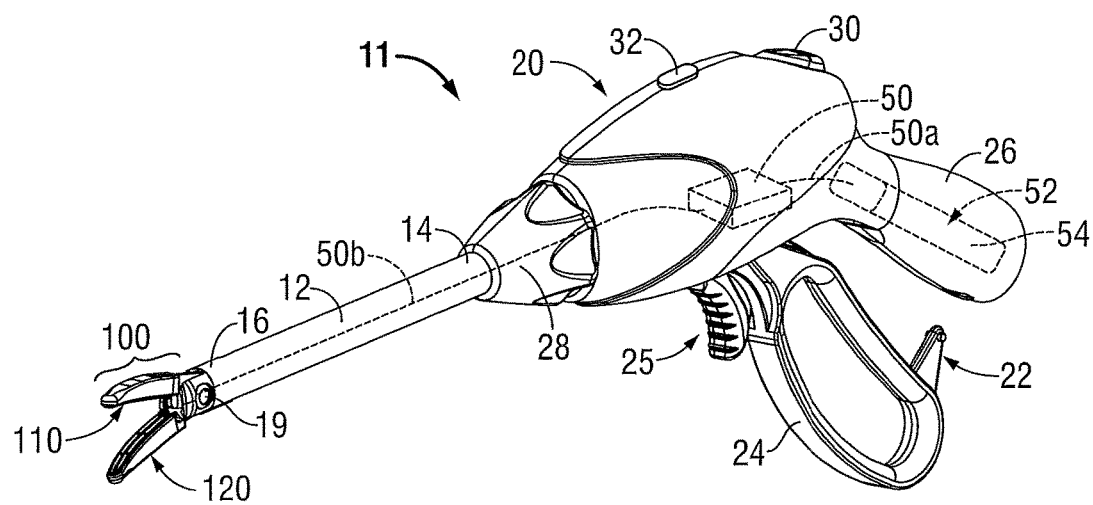
FIG. 1B is a perspective view of a battery-operated endoscopic forceps having an end effector assembly, which incorporates all or a portion of the components of an OCT system, attached to a distal end of the forceps according to another embodiment of the present disclosure.

Referring now to FIG. 1B, forceps 11 is shown having a portable configuration and includes an internal generator 50 for generating energy that is operably coupled to a battery compartment 52 via one or more wires 50a. In some embodiments, one or more battery operated laser diodes or fiber lasers may also be used to provide a portable light energy source. The internal generator 50 may be configured to provide energy to the end effector assembly 100. The battery compartment 52 may be configured to receive one or more batteries 54 for providing suitable energy to internal generator 50. In embodiments, the controller 42 may also be disposed within the forceps 11 (e.g., the housing 20).

Battery compartment 52 may be defined within any suitable portion of housing 20 of forceps 11, such as the fixed handle 26, as shown in FIG. 1B. Suitable batteries may include, but are not limited to a nickel-cadmium, lithium-ion, rechargeable, or any other suitable type. The location of internal generator 50 provides an operator increased maneuverability and convenience when performing a surgical treatment with forceps 11.

Figure 2:
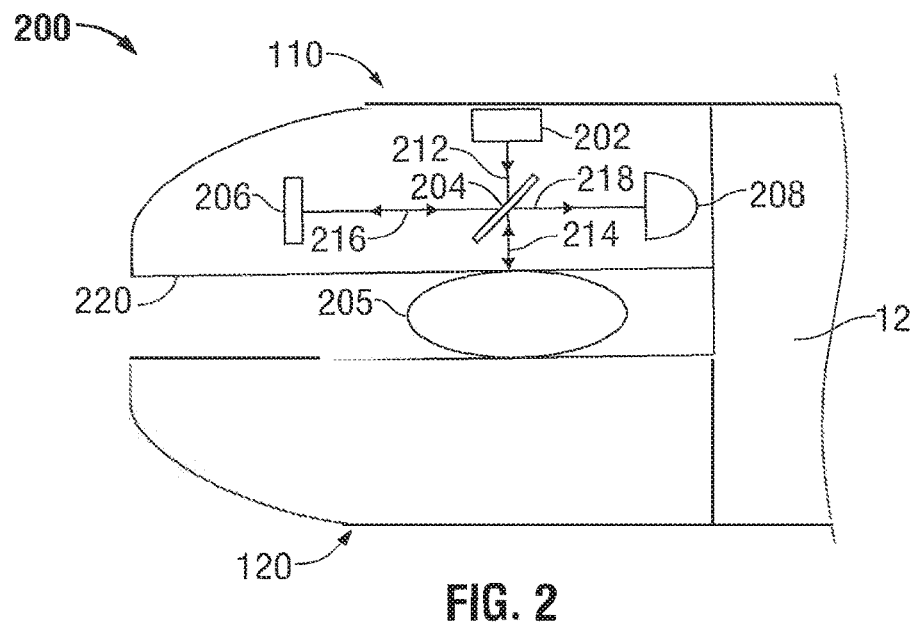
FIG. 2 is a schematic side, cross-sectional view of an end effector assembly incorporating optical components of an OCT system according to embodiments of the present disclosure.

FIG. 2 illustrates an end effector assembly 100 according to some embodiments of the present disclosure, which is configured for use with either surgical instrument 10 or surgical instrument 11 described above or any other suitable surgical instruments. However, for purposes of simplicity and consistency, end effector assembly 100 is described below with reference to instrument 10.

The end effector assembly 100 includes a first jaw member 110 that incorporates a free-space OCT system 200. The OCT system 200 includes a light source 202, a beamsplitter 204, a reference mirror 206, and a light detector 208. The light source 202 is electrically coupled to the generator 40 to receive power and/or command signals from the generator 40. The light detector 208 is electrically coupled the generator 40 to provide light detection signals to the generator 40 and to receive power from the generator 40.

In operation, the light source 202 (e.g., a monochromatic light source) emits a source beam 212 toward the beamsplitter 204, which is positioned diagonally with respect to the source beam 212. The beamsplitter 204 splits the source beam 212 into two halves: a first beam 214 and a second beam 216. The first beam 214 is transmitted through the beamsplitter 204 and then is reflected back from the tissue 205 towards the beamsplitter 204. The second beam 216 is reflected off the beamsplitter 204 and then is reflected back towards the beamsplitter 204 by the reference mirror 206. The back-reflected first beam 214 and the back-reflected second beam 216 are recombined by the beamsplitter 204 into a recombined beam 218 that is detected by the light detector 208. The light detector 208 then transmits an electrical signal representing the detected recombined beam 218 to the generator 40, which detects an interference pattern based on the electrical signal and displays an image of the tissue 205 based on the detected interference pattern.

Figure 3:
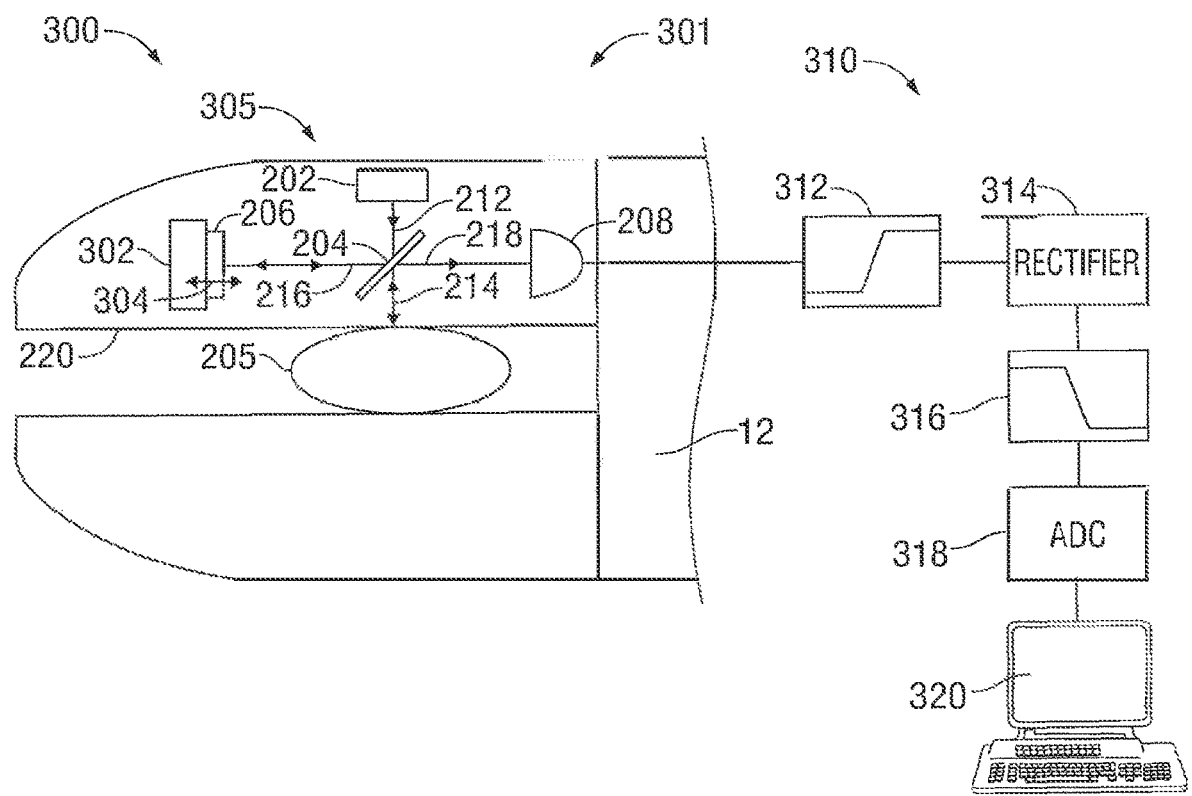
FIG. 3 is a schematic diagram of a surgical system incorporating an OCT system according to other embodiments of the present disclosure.

FIG. 3 is a schematic diagram of a surgical system 300 incorporating an OCT system having an optical assembly 305 and an electrical assembly 310. As shown, the surgical system 300 includes an end effector assembly 301 that incorporates the optical assembly 305 and the electrical assembly 310. The configuration of the optical assembly 305 is similar to the configuration of the optics in FIG. 2, except that the reference mirror 206 is disposed on a movable element 302 that can move the reference mirror 206 along a horizontal axis 304 to perform scanning of the tissue.

FIG. 3 also illustrates the electrical assembly 310 of the OCT system that receives the interference signal generated by the light detector 208. The electrical assembly 310 may be disposed in the generator of FIG. 1. The electrical assembly 310 includes an amplifier 312, a demodulator 314, and an analog-to-digital converter (ADC) 316. The amplifier 312 amplifies the light detector signals and the demodulator 314 demodulates the amplified signals as the reference mirror 206 is moved along a horizontal axis 304. The demodulator 314 provides scan signals to the ADC 316, which converts the scan signals into digital scan data. The digital scan data are then provided to a computer system 320 that generates an image that is displayed on the display of the computer system 320. In addition or in the alternative, the computer system 320 may analyze the digital scan data to identify the tissue, to determine the status of the tissue being sealed, or to determine that quality of a tissue seal.

In some embodiments, the computer system 320 may be incorporated into the forceps 11 of FIG. 1B. For example, the processor of the computer system 320 may be incorporated into the internal generator 50 of the forceps 11 and a display of the computer system 320 may be disposed on the housing 20 of the forceps 11.

Figure 4:
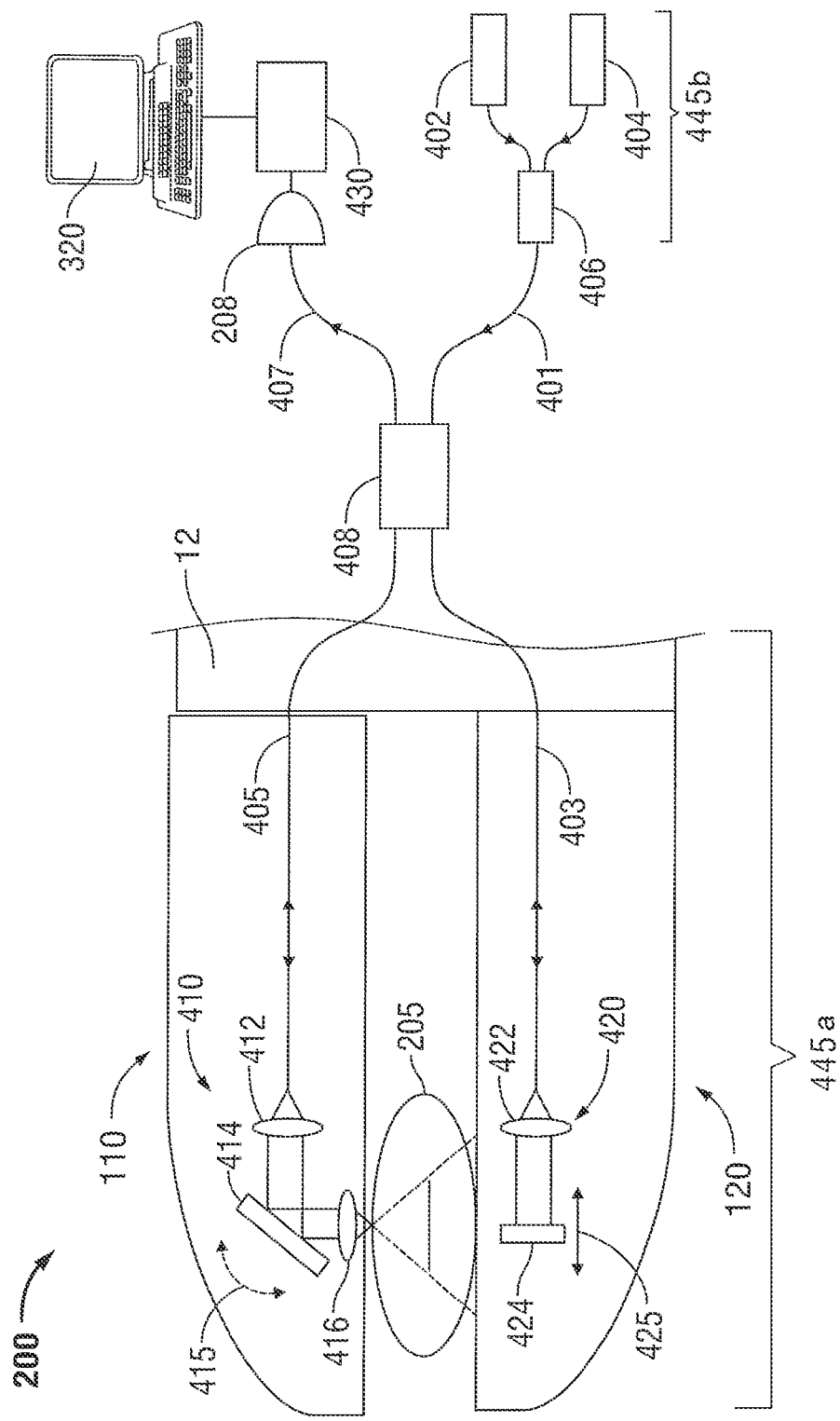
FIG. 4 is a schematic diagram of a surgical system incorporating a fiber-optic OCT system according to yet other embodiments of the present disclosure.

FIG. 4 is a schematic diagram of a surgical system 400 incorporating a fiber-optic OCT system. A first portion 445a of the fiber-optic OCT system is incorporated into the jaw members 110, 120 of the end-effector assembly 440. The first portion 445a of the fiber-optic OCT system includes a sample arm 410, which is incorporated into the first jaw member 110, and a reference arm 420, which is incorporated into the second jaw member 120. Alternatively, the reference arm 420 may be incorporated into the generator 40 of FIG. 1A.

A second portion 445b of the fiber-optic OCT system is disposed outside of the end-effector assembly 440. In some embodiments, the second portion 445b of the fiber-optic OCT system is disposed in the generator 40 of FIG. 1A. In other embodiments, the second portion 445b of the fiber-optic OCT system is disposed in the internal generator 50 of FIG. 1B.

As shown in FIG. 4, the second portion 445b of the fiber-optic OCT system includes two light sources: an imaging light source 402 and a visible light source 404. The imaging light source 402 may be a broadband source (e.g., a broadband, near-infrared source) that generates an imaging beam to image tissue. Examples of broadband sources include super-luminescent diodes, fiber amplifiers, and femto-second pulse lasers that generate light having a wavelength that ranges between 800 and 1550 nanometers. The visible light source 404 generates a visible aiming beam. The outputs of the imaging light source 402 and the visible light source 404 are optically coupled to a 2×1 optical coupler 406, which combines the imaging light beam with the visible light beam so that a user can see the imaging light beam.

The light output from the 2×1 optical-fiber coupler 406 is coupled into optical fiber 401 of the fiber-optic interferometer. The light is split into two optical fibers—a reference arm optical fiber 403 and a sample arm optical fiber 405—using a 2×2 optical-fiber coupler 408. The reference arm optical fiber 403 is optically coupled to reference arm optics 420. The reference arm optics 420 includes a lens 422, such as a convex lens, and a reference mirror 424. The lens 422 forms a light beam from the light emitted from the reference arm optical fiber 403 and directs it to the reference mirror 424. The light reflects off the reference mirror 424 and travels back towards the optical-fiber coupler 408 through the lens 422 and the reference arm optical fiber 403.

A sample arm optical fiber 405 is coupled to the sample arm optics 410, which transmits light to the tissue 205. The light is reflected from the tissue 205 back into the sample arm optical fiber 405. The light is reflected from the tissue as a result of changes in the index of refraction within the structure of the tissue, e.g., between intercellular fluid and collagen fibers. The light reflected back from the tissue 205 and the light reflected back from the reference mirror 424 are recombined within the 2×2 fiber-optical coupler 408.

Because of the short coherence length of the broadband light source 402, the light reflected from the tissue and the light reflected from the reference mirror 424 will interfere constructively and destructively only if the optical path lengths of the sample arm 410 and the reference arm 420 are matched. By changing the length of the reference arm, the tissue can be sampled at various depths.

The light recombined by the 2×2 fiber-optical coupler 408 is provided to the optical detector 208, e.g., a photodiode via optical fiber 407. The optical detector 208 detects the interference between the light reflected from the tissue and the light reflected from the reference mirror 424. During OCT imaging, the reference mirror 424 is scanned along the longitudinal axis 425 A-A of the second jaw member 120 at a constant velocity, thus allowing depth scans of the tissue (analogous to ultrasound A-scans).

The sample arm optics 410 may be configured to perform lateral scans across the tissue to construct two- and three-dimensional images. In the embodiment shown in FIG. 4, the sample arm mirror 414 may be rotatable 415 about a transverse axis B-B of the first jaw member 110 to scan the tissue 205 along the longitudinal axis of the first jaw member 110. The detected interference signals from this scan are then used to construct a two-dimensional cross-sectional image of the tissue 205.

The optical detector 208 then transmits the detected interference signal to a processor 430, which forms an image of the tissue based on the detected interference signal. The image is then displayed on a computer display 320.

The surgical systems according to embodiments of the present disclosure may generate images of a region of tissue so that a surgeon can determine the status of the tissue after a sealing procedure. For example, the surgeon can use the generated images to verify whether or not the tissue has been sealed or to determine whether or not the tissue has been properly sealed.

Figure 5:
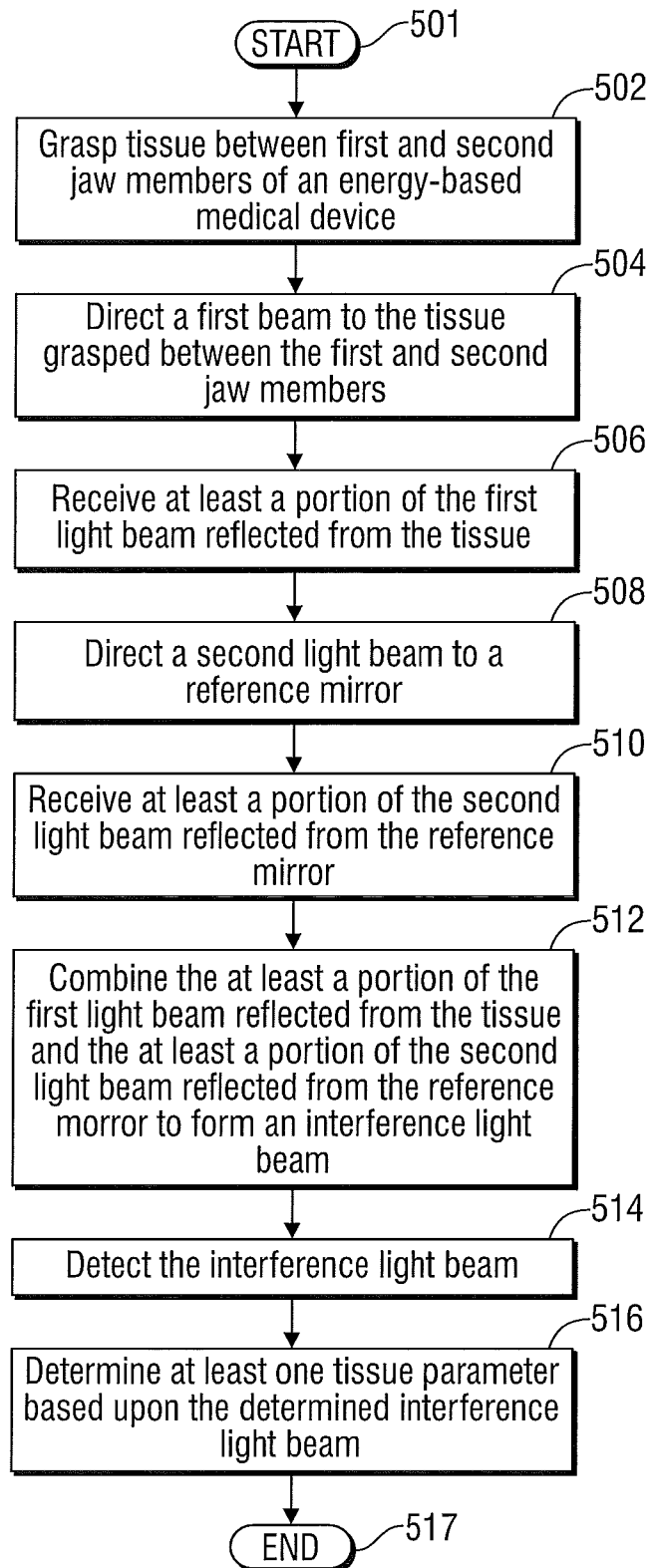
FIG. 5 is a flow diagram of a method of determining properties of tissue in an energy-based medical device according to embodiments of the present disclosure.

FIG. 5 is a flow diagram of a method for determining properties of tissue in an energy-based medical device according to embodiments of the present disclosure. After starting in step 501, tissue is grasped between first and second jaw members of an energy-based medical device in step 502. In step 504, a first light beam is directed to the tissue grasped between the first and second jaw members and, in step 506, at least a portion of the first light beam reflected from the tissue is received, e.g., by a light detector. In step 508, a second light beam is directed to a reference mirror, and, in step 510, at least a portion of the second light beam reflected from the reference mirror is received, e.g., by the light detector.

In step 512, at least a portion of the first light beam reflected from the tissue and at least a portion of the second light beam reflected from the reference mirror are combined to form an interference light beam. Finally, before ending in step 517, the interference light beam is detected in step 514 and one or more tissue properties are determined based upon the detected interference light beam in step 516. The tissue properties may include tissue type, cell type, disease state, or disease pathology.

As described herein, the energy-based medical devices may have an OCT probe embedded within the jaw members or the OCT probe may a retractable probe that is deployed from the shaft of the medical device. In these configurations, the OCT imaging may be performed prior to energy delivery when the jaw members clamp onto unsealed tissue, to determine the structural density of the tissue. The structural density information would then be relayed to a controller to adjust the temperature and/or energy to perform a tissue seal. The OCT imaging may also be performed after performing a tissue sealing procedure so that the clinician can determine the success and/or quality of the tissue seal. This type of imaging/sealing medical device would be beneficial when sealing large vessels and thick tissue masses.

The OCT imaging may be used in combination with any type of energy-based medical device including medical devices that treat tissue using light energy, radio frequency energy, or ultrasound energy.

Figure 6:
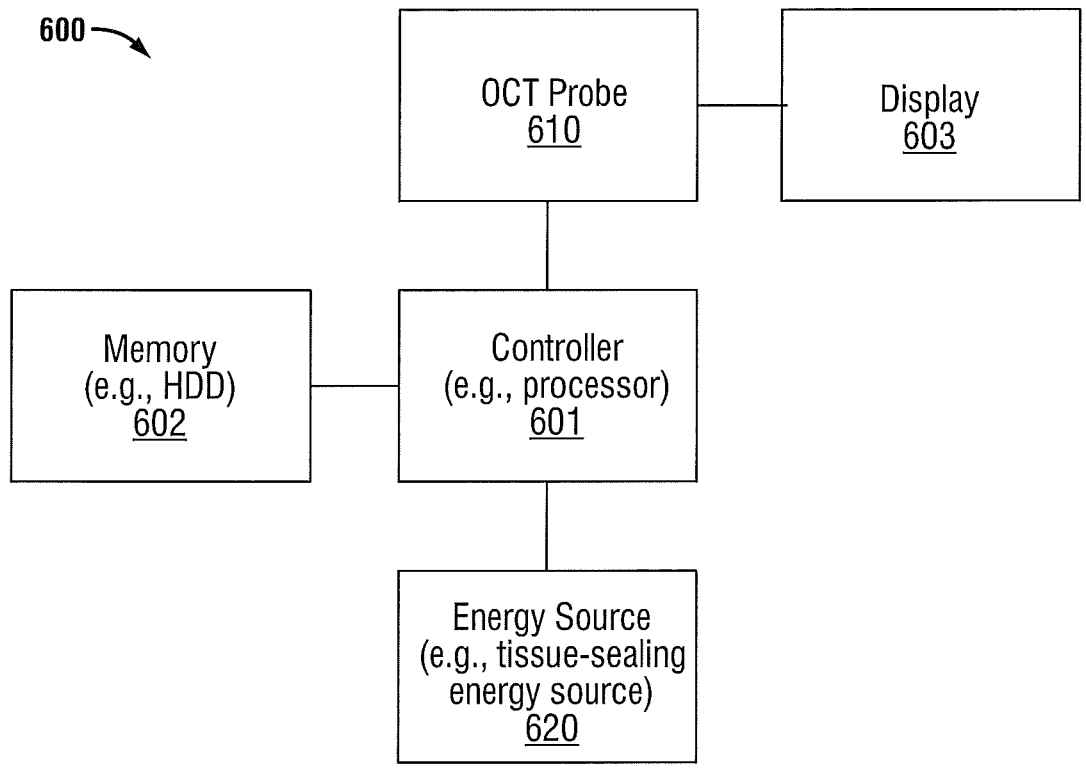
FIG. 6 is a schematic diagram of a surgical system according to embodiments of the present disclosure.

FIG. 6 is a schematic diagram of surgical system 600 that incorporates an OCT probe. The surgical system 600 includes a controller 601, a memory 602, a display 603, an OCT system 610, and a generator or energy source 620. The controller 601 is electrically connected to the energy source 620 to control the energy output from the energy source 620. The energy source 620 may output light energy, electrical energy, or ultrasonic energy. The controller 601 controls the amount of energy output from the energy source 620 to achieve a desired tissue effect. For example, in the case that the energy source 620 is a light energy source, the controller 601 controls the intensity and/or other properties of the light energy, e.g., polarization, to seal tissue that is placed between the jaws of a surgical device.

According to the present disclosure, the controller 601 is electrically connected to the OCT system 610 to receive optical feedback information, which is used by the controller 601 to adjust the properties of the energy output from the energy source 620. The optical feedback information includes images that indicate the structural density and/or other properties of the tissue that is placed between the jaws of a surgical instrument. As described herein, all or a portion of the surgical system 600 may be incorporated into a surgical instrument. For a portable surgical instrument, all of the components of the surgical system 600 may be incorporated into the surgical instrument.

The controller 601, which may be a processor, a digital signal processor, a central processing unit (CPU), or microprocessor, is coupled to the memory 602, which may be a non-volatile memory such as ROM or NVRAM. The controller 601 may retrieve instructions from the memory 602 and may execute the instructions to control the energy source 620 based on feedback from the OCT system 610.

The OCT system 610 may be coupled to a display 603 that displays images of the tissue obtained by the OCT system 610. The display 603 may allow for an operating mode in which a user may manually adjust the amount of energy output from the energy source 610 as the user views the display 603.

According to the present disclosure, the OCT probe may be embedded in a jaw member of a tissue-sealing surgical device, e.g., an optical vessel sealer, which allows for imaging of tissue to be performed before and after the tissue seal without device reconfiguration. The jaw member may include a transparent window disposed at or near the tissue-contacting surface of the jaw member to allow for imaging of tissue disposed between the jaw members of the tissue-sealing surgical device.

Figure 7:
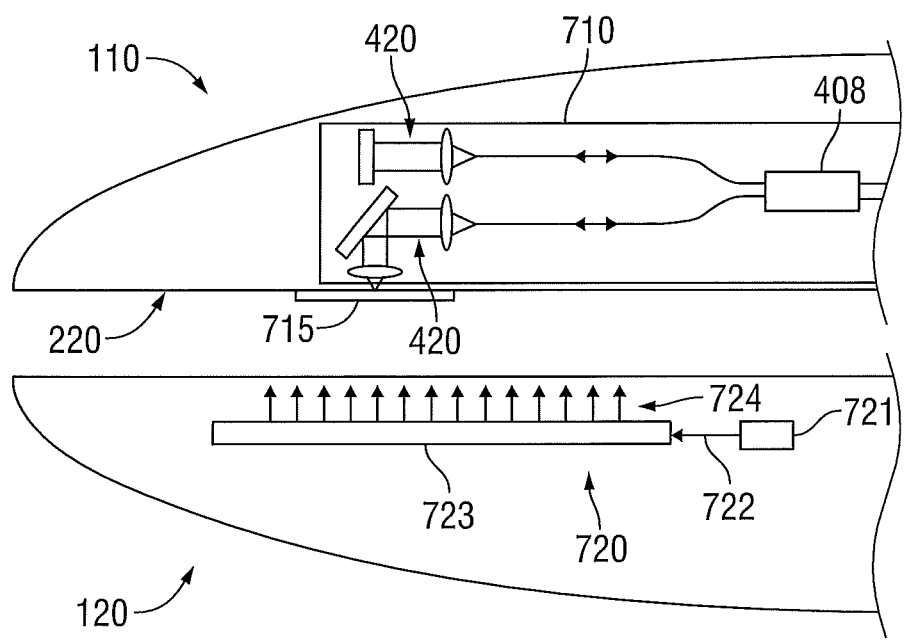
FIG. 7 is a schematic diagram of a surgical system incorporating a fiber-optic OCT system and a light energy delivery system according to embodiments of the present disclosure.

FIG. 7 is a schematic diagram of a surgical system incorporating a fiber-optic OCT probe 710 and a light-energy delivery system 720. The fiber-optic OCT probe 710 is incorporated into the first jaw member 110 and the light-energy delivery system 820 is incorporated into the second jaw member 120. The fiber-optic OCT probe 710 incorporates similar components as the fiber-optic OCT system shown in FIG. 4. The fiber-optic OCT probe 710 includes a sample arm 410 and a reference arm 420 and an optical coupler 408. The OCT probe 710 may be optically coupled to the remaining components of an OCT system, which are illustrated above in FIG. 4.

The light-energy delivery system 720 includes a light source 721, an optical fiber or other light waveguide 722, and a light distribution element 723. The light source 721 generates light having an appropriate intensity and wavelength for sealing or otherwise treating tissue disposed between the jaw members 110 and 120. The optical fiber 722 carries the light generated by the light source 721 to the light distribution element 723, which forms and distributes a light beam perpendicular to or substantially perpendicular to the tissue-contacting surface of the second jaw member 120.

A method of using the surgical system of FIG. 7 may include grasping tissue between the first and second jaw members 110 and 120, sensing optical properties of the tissue using the OCT probe 710, and delivering light to tissue using the light-energy delivery system 720 based on the sensed optical properties of the tissue.

Vessels containing large and small amounts of collagen show differences in structural density. Specifically, vessels with large collagen content have greater structural density than vessels with low collagen content. Thus, OCT may be used to detect the structural density of vessels, which may then be correlated to collagen content.

Preliminary testing has shown that vessels with a large amount of collagen content (e.g., the carotid artery) are more consistently sealed than vessels with low collagen content (e.g., the femoral artery). Since collagen has a lower denaturation temperature than elastin, tissues with higher collagen content may form seals at lower temperatures. Thus, OCT may be used to determine the collagen or elastin content of tissue, and the amount of energy delivered to the tissue may be controlled based on the collagen or elastin contents of the tissue.

For example, OCT may be used to determine the amount of collagen and/or elastin in a vessel disposed between the jaw members 110 and 120. If the OCT probe 710 senses a large amount of collagen in the vessel, then the light-energy delivery system 720 may deliver less energy to the vessel as compared to another vessel having a smaller amount of collagen because collagen has a lower denaturation temperature.

The tissue-contacting surface 220 of the first jaw member 110 may be coated with a reflective layer 715 adjacent the light output of the sample arm 410 of the fiber-optic OCT probe 710 so that the light beam from the light-energy delivery system 720 does not damage the components of the fiber-optic OCT probe 710.

In another mode of operation, the OCT probe 710 and the light-energy delivery system 720 may be operated simultaneously. In other words, the OCT probe 710 may sense optical properties of the tissue while the light-energy delivery system 720 is delivering light to the tissue. In this mode of operation, a controller (not shown) coupled to the light-energy delivery system 720 may control the intensity of the light produced by the light-energy delivery system 720.

Figure 8A:
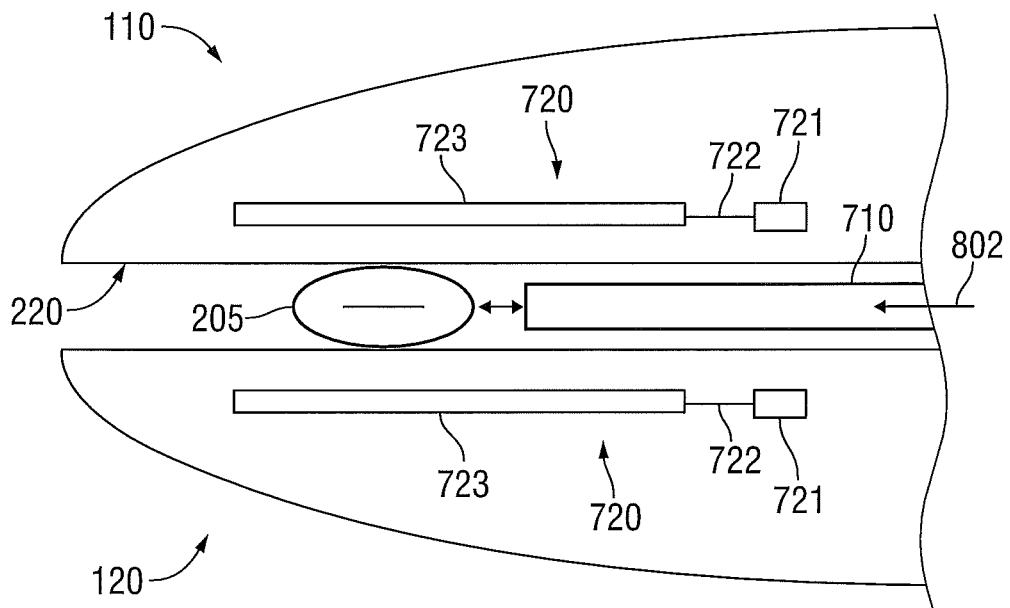
FIGS. 8A and 8B are schematic diagrams of surgical systems incorporating a fiber-optic OCT system and a light energy delivery system according to other embodiments of the present disclosure.
Figure 8B:
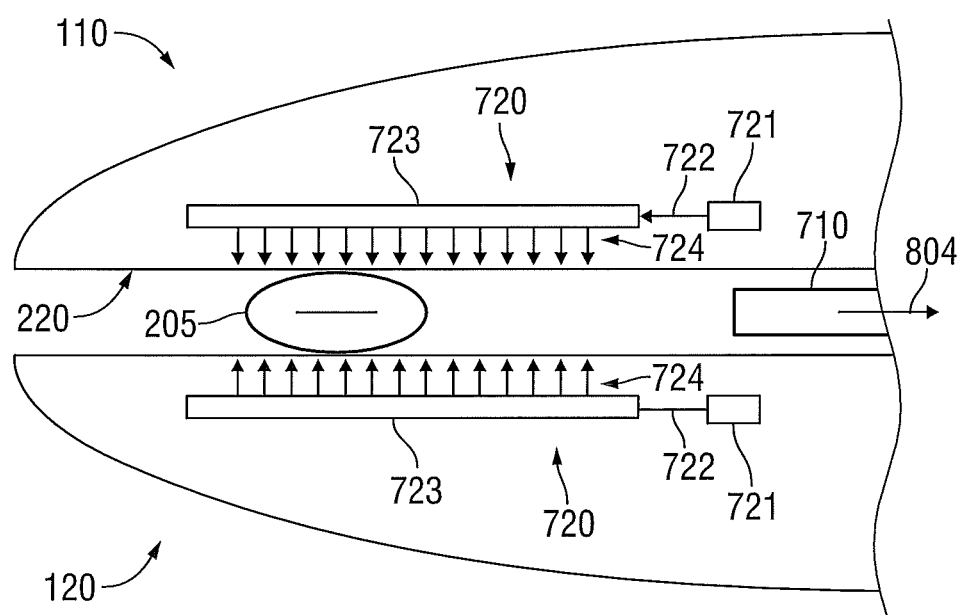

FIGS. 8A and 8B are schematic diagrams of a surgical system incorporating light-energy delivery systems 720 into both the first and second jaw members 110 and 120. Specifically, each of the first and second jaw members 110 and 120 includes a light source 721, an optical fiber or waveguide 722, and a light distribution element 723. The OCT probe 710 is movably coupled to the surgical device so that it can be inserted into and remove from between the first and second jaw members 110 and 120.

In an example mode of operation, tissue is grasped between the first and second jaw members 110 and 120 of a surgical device. Next, the OCT probe 710 is inserted 802 in between the first and second jaw members 110 and 120 so that the distal end of the OCT probe 710 is disposed adjacent to the tissue. Then, the OCT probe is operated to sense the properties of the tissue disposed between the first and second jaw members. A controller (not shown) coupled to the OCT probe 710 may determine parameters for light energy based upon the properties of the tissue sensed by the OCT probe 710.

Next, as illustrated in FIG. 8B, the OCT probe 710 is removed 804 from in between the first and second jaw members 110 and 120. Then, the controller (not shown) may operate the light-energy delivery systems 720 according to the determined parameters for the light energy. The controller may operate the light-energy delivery systems 720 so that they simultaneously and/or alternatively deliver light to the tissue.

In other embodiments, the light energy delivery systems 723 may be replaced by other energy delivery systems such as ultrasonic or electrical energy delivery systems. These alternative energy delivery systems may be operated in the same manner as described above with respect to the light energy delivery systems 720.

Figure 9:
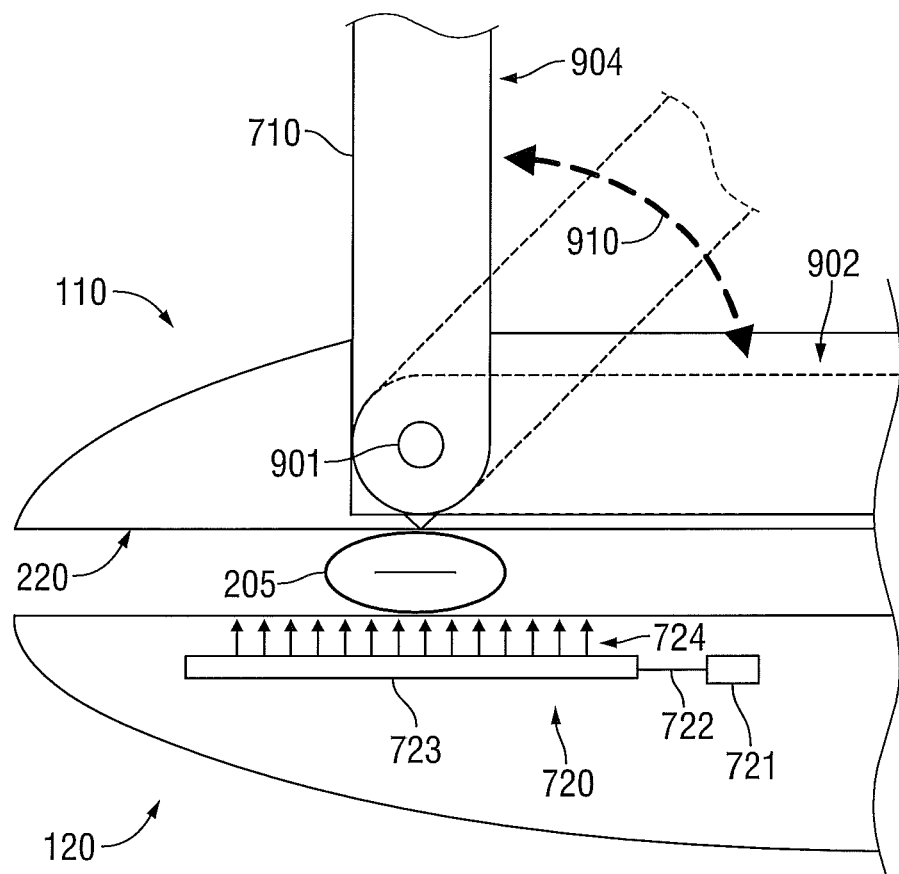
FIG. 9 is a schematic diagram of a surgical system incorporating a fiber-optic OCT system and a light energy delivery system according to yet other embodiments of the present disclosure.

FIG. 9 is a schematic diagram of a surgical system incorporating the light energy delivery system 720 and a rotatable OCT probe 710. As shown in FIG. 9, the OCT probe 710 is rotatable 910 about the pin 901 from a first position 902 to a second position 904. The first position 902 may be a position at which the OCT probe 710 is not used and the second position 904 may be a position at which the OCT probe 710 is operated to sense properties of the tissue disposed between the jaw members 110 and 120.

Thus, according to one method of operation, the first and second jaw members 110 and 120 are operated to grasp tissue 205 and the OCT probe 710 is rotated from the first position 902 to the second position 904. Then, the OCT probe 710 is operated to sense properties of the tissue 205. After the OCT probe 710 senses the properties of the tissue 205, the OCT probe 710 may be rotated back to the first position 902 before the light-energy delivery system 720 delivers light to the tissue 205. Alternatively, the OCT probe 710 may remain in the second position 904 while the light-energy delivery system 720 delivers light to the tissue 205. Then, the light-energy delivery system 720 delivers light to the tissue 205.

Figure 10:
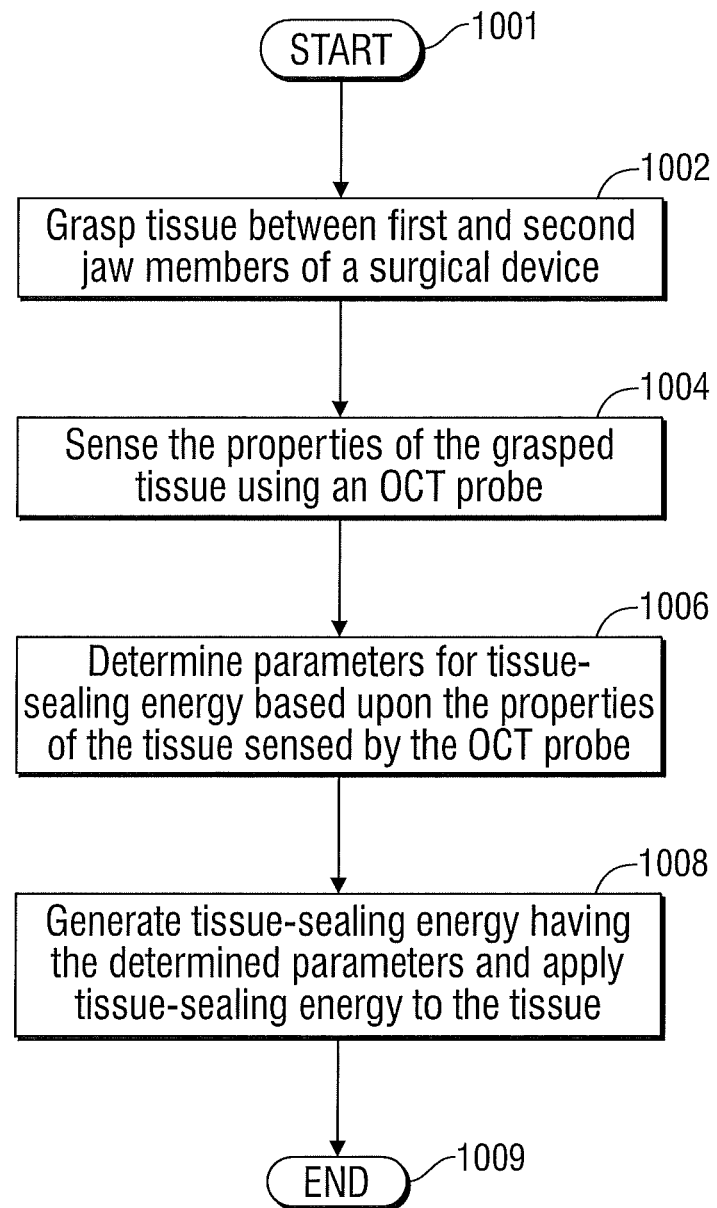
FIG. 10 is a flow diagram of a method of sealing tissue with an energy-based medical device according to embodiments of the present disclosure.

FIG. 10 is a flow diagram of a method of sealing tissue using an energy-based surgical device. After starting in step 1001, tissue is grasped between the first and second jaw members of the surgical device in step 1002. In step 1004, the properties of the tissue disposed between the first and second jaw members are sensed using an OCT probe. The sensed properties of the tissue may include the structural density or structural profile of the tissue.

In step 1006, parameters of tissue-sealing energy are determined based upon the properties of the tissue sensed by the OCT probe. These parameters may include power, voltage, and/or current in the case of electrosurgical and ultrasonic surgical devices. In the case of light-based surgical devices, the parameters may include intensity, frequency, wavelength, and/or polarization. The parameters may also include temperature.

For example, if the OCT probe senses a high structural density of vascular tissue disposed between the first and second jaw members, which indicates a large concentration of collagen within the vascular tissue, the intensity and wavelength of a light beam generated by a light-based surgical instrument may be controlled so that a sufficient amount of light energy is provided to the vascular tissue to denature the collagen within the vascular tissue.

Before the method ends in step 1009, tissue-sealing energy having the determined parameters is generated and applied to the tissue.

Figure 11:
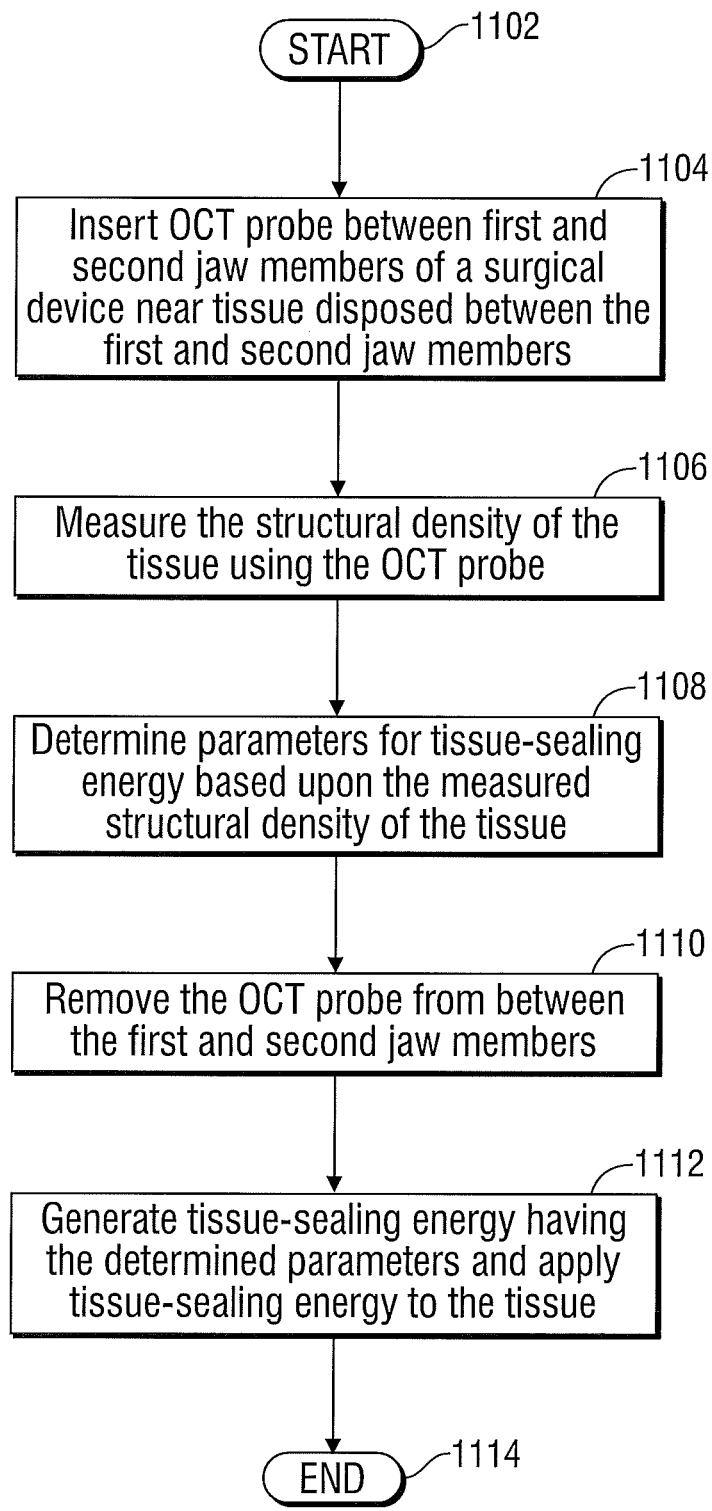
FIG. 11 is a flow diagram of a method of sealing tissue with an energy-based medical device according to other embodiments of the present disclosure.

FIG. 11 is a flow diagram of another method of sealing tissue using an energy-based surgical device. After starting, in step 1102, an OCT probe is inserted between first and second jaw members of a surgical device near tissue disposed between the first and second jaw members, in step 1104. In step 1106, the structural density of the tissue disposed between the first and second jaw members are measured using the OCT probe. In step 1108, parameters for tissue-sealing energy to be applied to the tissue are determined based upon the structural density of the tissue measured in step 1106.

After determining the parameters for the tissue-sealing energy to be applied to the tissue in step 1108, the OCT probe is removed from between the first and second jaw member in step 1110 so that the probe is not exposed the tissue-sealing energy. Then, before the method ends in step 1114, tissue-sealing energy having the determined parameters is generated and applied to the tissue.

The OCT systems described above may be modified to monitor different properties of tissue. For example, the sample arm optics 410 and the reference arm optics 420 of the OCT system could incorporate polarization-altering optics (e.g., polarized lenses, plates, or windows) to determine the tissue birefringence based upon the magnitude of the back-reflected light.

The OCT systems may be configured to perform optical coherence microscopy for histology or tissue diagnostics. The OCT system may incorporate optical elements to achieve resolutions comparable to confocal microscopy but with increased depth of penetration. For example, the OCT system may incorporate optical elements having a high numerical aperture (e.g., the lens 416 may have a high numerical aperture) to achieve high resolutions and a large penetration depth.

The surgical systems of the present disclosure (e.g., the surgical system 400 of FIG. 4) may incorporate mechanisms for selectively applying different optical elements to achieve different optical effects. In some embodiments, the surgical system 400 may include a mechanism that switches between a standard optical element (e.g., the lens 416) and an optical element having a high numerical aperture. In other embodiments, a polarization-altering optical element may be inserted in series with the standard optical element (e.g., the lens 416).

In other embodiments, the OCT systems may be configured to perform color Doppler optical coherence tomography (CDOCT) to measure tissue perfusion, i.e., the amount of blood that flows through tissue.

While several embodiments of the disclosure have been shown in the drawings and/or discussed herein, it is not intended that the disclosure be limited thereto, as it is intended that the disclosure be as broad in scope as the art will allow and that the specification be read likewise.

Therefore, the above description should not be construed as limiting, but merely as exemplifications of particular embodiments. Those skilled in the art will envision other modifications within the scope and spirit of the claims appended hereto.

What is claimed is:

1. A surgical system comprising:
a housing;
an end effector assembly operably coupled to the housing, the end effector assembly including:
first and second jaw members each having a tissue contacting surface, at least one of the first or second jaw members movable between a first, spaced-apart position and a second grasping position;
a light source within the first jaw member and configured to provide a source beam;
a reference mirror within the first jaw member; and
a beamsplitter within the first jaw member and optically coupled to the light source, the beamsplitter positioned and configured to:
receive the source beam from the light source and split the source beam into a first beam and a second beam,
direct the first beam to tissue grasped between the first and second jaw members and receive a back-reflected first beam comprising at least a portion of the first beam reflected from the tissue,
direct the second beam to the reference mirror and receive a back-reflected second beam comprising at least a portion of the second beam reflected from the reference mirror,
combine the received back-reflected first beam and the received back-reflected second beam to form a recombined beam, and
direct the recombined beam to a light detector; and
a processor configured to process a signal based on the recombined beam and obtain interference pattern data.

2. The surgical system according to claim 1, wherein the end effector assembly further includes a movable element configured to move the reference mirror to scan the tissue.

3. The surgical system according to claim 2, wherein the light detector provides an electrical signal representing the recombined beam.

4. The surgical system according to claim 3, further comprising an amplifier configured to amplify the electrical signal representing the recombined beam to provide an amplified signal.

5. The surgical system according to claim 4, further comprising a demodulator configured to demodulate the amplified signal as the reference mirror is moved to scan the tissue, the demodulator providing scan signals.

6. The surgical system according to claim 5, further comprising an analog-to-digital converter configured to converts the scan signals to digital scan data, wherein the digital scan data is the signal processed by the processor.

7. The surgical system according to claim 6, wherein the processor is further configured to generate an image based on the digital scan data.

8. The surgical system according to claim 6, wherein the processor is further configured to identify the tissue based on the digital scan data.

9. The surgical system according to claim 6, wherein the processor is further configured to determine a status of the tissue being sealed based on the digital scan data.

10. The surgical system according to claim 6, wherein the processor is further configured to determine a quality of a tissue seal based on the digital scan data.

11. The surgical system according to claim 4, wherein the second beam is reflected off the beamsplitter.

12. The surgical system according to claim 1, further comprising a forceps comprising the the housing, the end effector assembly, and the processor.

13. The surgical system according to claim 12, further comprising a display disposed on the housing.

14. The surgical system according to claim 1, wherein the first beam is transmitted through the beamsplitter.

15. A surgical system comprising:
a first jaw member and a second jaw member each having a tissue contacting surface, at least one of the first or second jaw members movable between a first spaced-apart position and a second grasping position, the first jaw member including:
a light source within the first jaw member and configured to provide a source beam;
a reference mirror within the first jaw member; and
a beamsplitter within the first jaw member and optically coupled to the light source, the beamsplitter positioned and configured to:
receive the source beam from the light source and split the source beam into a first beam and a second beam,
direct the first beam to tissue grasped between the first and second jaw members and receive a back-reflected first beam comprising at least a portion of the first beam reflected from the tissue,
direct the second beam to the reference mirror and receive a back-reflected second beam comprising at least a portion of the second beam reflected from the reference mirror,
combine the received back-reflected first beam and the received back-reflected second beam to form a recombined beam, and
direct the recombined beam to a light detector; and
a processor configured to process a signal based on the recombined beam and obtain interference pattern data.

16. The surgical system according to claim 15, further comprising:
an energy source coupled to at least one of the first and second jaw members, the energy source configured to deliver energy to at least one of the first jaw member or the second jaw member to seal tissue; and
a controller coupled to the light detector and the energy source, the controller configured to control the energy source based on at least one measured property of light passing through the tissue.

17. The surgical system according to claim 15, wherein at least one of the energy source or the controller are disposed within a housing coupled to the first and second jaw members.

* * * * *